United States Patent [19]

Belkin et al.

[11] 4,413,890

[45] Nov. 8, 1983

[54] INSTRUMENT FOR OBJECT DETECTION OF OCULAR DISEASES

[76] Inventors: Michael Belkin, 12 Alexander Yanai St., Tel-Aviv, Israel; David J. Lund, 60 McKeon Ct., Novato, Calif. 94947

[21] Appl. No.: 245,655

[22] Filed: Mar. 20, 1981

[51] Int. Cl.³ .............................................. A61B 3/10
[52] U.S. Cl. .................................. 351/221; 351/211; 351/205
[58] Field of Search ..................... 351/6, 13, 16, 14, 9, 351/7, 11

[56] References Cited

U.S. PATENT DOCUMENTS

| | | |
|---|---|---|
| 3,450,466 | 6/1969 | Streisinger . |
| 3,524,702 | 8/1970 | Bellows .................................. 351/6 |
| 3,614,214 | 10/1971 | Cornsweet et al. . |
| 3,639,941 | 2/1972 | Cornsweet ............................ 351/14 |
| 3,791,719 | 2/1974 | Kratzer ................................. 351/11 |
| 3,819,256 | 6/1974 | Bellows ................................. 351/6 |
| 3,827,789 | 8/1974 | Molner et al. . |
| 3,915,564 | 10/1975 | Urban . |
| 4,305,398 | 12/1981 | Sawa . |

Primary Examiner—John K. Corbin
Assistant Examiner—Rodney B. Bovernick
Attorney, Agent, or Firm—Cushman, Darby & Cushman

[57] ABSTRACT

An apparatus for objectively detecting ocular disorders adapted to the expedient examination of uncooperative patients generally comprises structures for collimating light into two predetermined paths for coaxial illumination of a person's right and left eye; structures for conditioning the collimated light; apertures for illuminating and retroflecting the collimated light by a person's eyes; and structures for detecting the relative intensities of the retroflected collimated light. A method for expediently examining uncooperative patients adapted to objectively detecting an ocular disorder comprises coaxially illuminating each eye; effecting a relative position between the apertures of an apparatus and a patient'eyes so that brief illuminating contact with the collimated light is effected; retroflecting the collimating light illuminating each eye; and measuring the relative intensities of the retroflected collimated light so that ocular disorders can be objectively determined.

19 Claims, 2 Drawing Figures

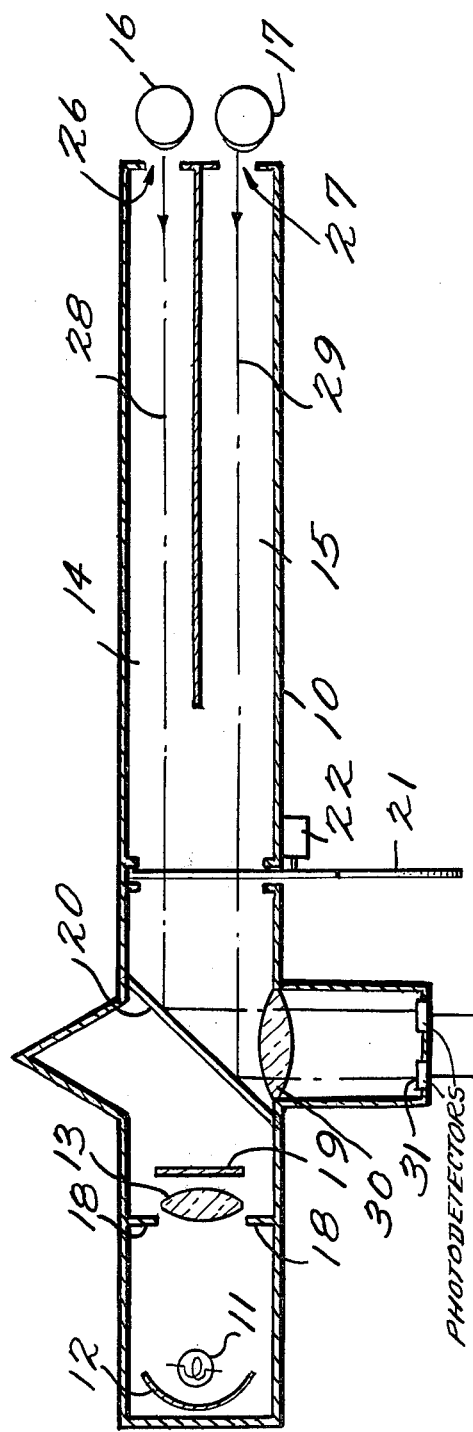
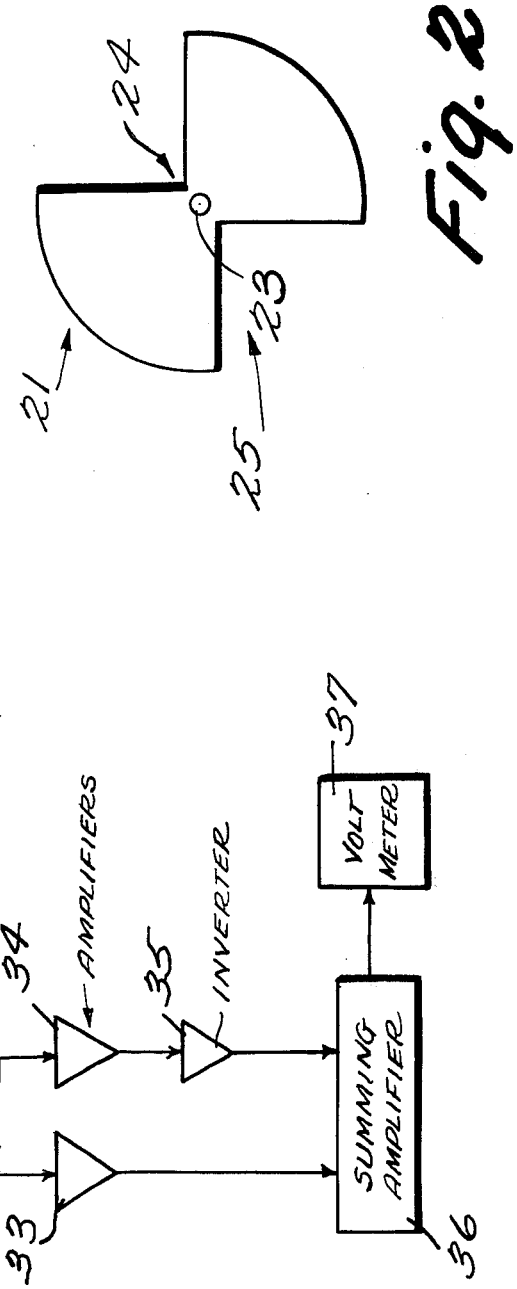

INSTRUMENT FOR OBJECT DETECTION OF OCULAR DISEASES

BACKGROUND AND SUMMARY OF THE INVENTION

This invention generally relates to the problems of detecting ocular disorders effectively and reliably in a patient. More specifically, this invention is concerned with the objective detection of ocular disorders so that uncooperative patients such as, for example, infants, pre-school children, infirm persons or the like can be expediently examined for ocular disorders and diseases.

Conventional devices which measure the depth of the optic fundus have been proposed, such as, for example, those disclosed in U.S. Pat. Nos. 3,524,702; 3,639,041; 3,791,719; and 3,819,256. The conventional devices for measuring the fundus depth of an eye utilize the general principle of retroflecting collimated light to determine the refractive index of the eye. However, most conventional devices utilize a complicated system of lenses together with either a mechanical or electrically operated focusing system. The additional elements provided in the conventional devices necessarily increase the cost of providing the devices to ophthalmologists, optometrists, hospitals or the like.

Most conventional devices require that a patient being examined stare either into the device or at a fixation point for a period of time so that the proper fundus reflex can be determined. Therefore, the length of time necessary to provide an accurate reading utilizing conventional devices is not conducive to the examination of uncooperative patients, such as, for example, infants, pre-school children, infirm persons or the like.

Additionally, conventional devices basically utilize two separate systems for determining the refractive index of the patient's eyes. Thus, the number of operational components is necessarily increased by providing two separate systems in a single ophthalmological device. As noted above, an increase in the number of operational components will necessarily increase the cost of the device and, thus, could make such a device cost prohibitive for certain organizations, schools or the like.

According to the present invention, however, there is provided an apparatus and method which can objectively determine ocular disorders by measuring the relative intensities of coaxially retroflected collimated light from a patient's eyes. The apparatus and method according to the present invention only requires that a patient look into the apparatus for a brief period of time, thereby enabling the examining ophthalmologist, optometrist or technician to obtain an accurate detection of ocular disorders. The device according to the present invention is relatively simple and therefore, can be manufactured inexpensively when compared to conventional devices utilized for measuring the fundus reflex of the eye.

The fundus reflex observable in the pupils of the eye in a normal patient when the eyes are coaxially illuminated is equal if the patient's eyes are parallely aligned and structurally normal. Any deviation from the normal in either alignment or structure will manifest itself in abnormal and/or unequal fundus reflexes. The apparatus and method according to the present invention enables an ophthalmologist, optometrist or technician to objectively compare the fundus reflexes of each eye simultaneously so that most ocular abnormalties and disorders of the eye and visual system can be readily detected. Additionally, the apparatus and method of the present invention may be utilized with minimal cooperation of the ocular patient by requiring the patient to only look briefly into the apparatus.

The fundus light reflex of both eyes can be measured and compared so that most ophthalmic pathological disorders can be objectively detected. Any quality or deviation from the normal under test circumstances can be objectively measured when the patient suffers from the following general ophthalmic disorders: Strabismus; Anisometropia; Anisocoria; Nystagmus; Opacities and/or abnormal light transmission of the ocular refractive media as well as most other pathological conditions of the refractive media; Exophthalmus; Enophthalmus and other abnormal positions of the eyeball; and many retinal and choroidal diseases.

Therefore, according to the present invention an apparatus and method are provided that are particularly adapted for screening eye diseases and ocular disorders in infants, pre-school children, infirm persons and other uncooperative patients. The apparatus according to the present invention is relatively simple and can be easily and inexpensively manufactured so that a variety of organizations will be able to obtain the apparatus and administer the test method for early detection of ocular disorders. The device is constructed so that an ocular screening test can be performed by relatively unskilled persons after minimal training so that schools, clubs or other organizations can be equipped to detect any early signs of ocular disorders. Additionally, a device according to the present invention is provided which is easily and effectively operated to monitor changes and progress in the condition of an ocular patient. Further advantages of using a device and method according to the present invention will be readily apparent to those of ordinary skill in the art when examining the detailed description of the invention.

BRIEF DESCRIPTION OF THE DRAWINGS

FIG. 1 is a cross sectional view of the apparatus according to the present invention as viewed from above; and FIG. 2 is an elevational view of the light modulating structure utilized in the apparatus of FIG. 1.

DETAILED DESCRIPTION OF THE INVENTION

Referring now more specifically to FIG. 1 wherein a representative embodiment of the present invention is depicted in cross sectional view, the apparatus is generally enclosed by an enclosure 10 which houses the optical components of the present apparatus.

Light is emitted from a light source 11 located in the rear of the apparatus. Immediately behind light source 11, there is provided a reflector 12 which redirects the backward component of the light radiation toward a collimating lens 13. The collimating lens 13 collimates the light and directs the collimated light into two predetermined paths 14 and 15, respectively. Path 14 is utilized to illuminate the right eye 16 of an ocular patient while path 15 is utilized to illuminate the left eye 17 of the ocular patient. All light emitted from the light source 11 is directed through the collimating lens 13 by providing a baffle 18 which blocks all stray light radiation not transmitted through the collimating lens 13.

Optionally, there may be provided subsequent to the collimating lens 13 an optical filter 19, such as, for example, a band pass filter. The collimated light from the collimating lens 13 is transmitted to and is incident upon a beam splitter 20 positioned in the apparatus such that the collimated light is incident upon it at an angle of about 45°. The beam splitter 20 reflects about 50% of the incident collimated light and transmits about 50% of the collimated light therethrough.

Subsequent to the beam splitter 20 in the path of the collimated light, there is provided a wheel structure 21 which conditions the collimated light into a square wave modulation. The wheel structure 21 is positioned such that a portion extends into the path of the collimated light. Wheel structure 21 is rotated by a motor 22 attachably connected to the central point of the wheel structure 21. The wheel structure 21 can be more clearly seen in FIG. 2 wherein an elevational view of the wheel structure 21 is depicted. The motor 22 is connected to the central point 23 of the wheel structure 21. Additionally, a portion of the generally opposing quadrants 24 and 25, respectively, are removed so that the collimated light can be transmitted therethrough when the wheel structure 21 is rotated through the path thereof.

The square wave modulated collimated light is directed into predetermined paths 14, 15 and coaxially illuminates the right and left eye 16 and 17, respectively, of the ocular patient. The modulated beam is incident upon a plate having two apertures 26 and 27 corresponding to the right and left eye 16 and 17, respectively. The ocular patient is positioned such that the right eye is looking through aperture 26 and the left eye is looking through aperture 27 so that the modulated beam will coaxially illuminate both eyes.

The collimated light which is incident upon the ocular pupil of each eye is retroflected in a collimated beam generally depicted as lines 28 and 29, corresponding to the retroflected beam of the right and left eye 16 and 17, respectively. The retroflected beam is directed by the beam splitter 20 to an imaging lens 30 which images the retroflected beams onto photodetectors 31, 32. The photodetectors measure the relative intensities of the retroflected light beams 28, 29 and generate an electrical voltage signal which is directly proportional to the light intensities. The retroflected light from the right eye 16 is detected by the right photodetector 32 and the retroflected light from the left eye 17 is detected by the left photodetector 31.

The voltage signal from each photodetector 31, 32 is probably amplified by amplifiers 33, 34 and the voltage signal from the right amplifier 34 is inverted by an inverter 35. The inverted voltage signal from the inverter 35 and the voltage signal from the left amplifier 33 are summed by a summing amplifier 36. The resultant summed voltage signal is proportional to the difference in light intensity retroflected from the right eye 16 and the left eye 17. Thus, a negative voltage will result if the right eye 16 reflects more strongly while a positive voltage will result if the left eye 17 reflects more strongly and if the retroflected light beam intensities are equal, a null voltage will result. The varying voltage measurements can be displayed on a suitable device, such as, a null reading volt meter 37 connected to the summing amplifier 36.

It its broadest sense, the method of the present invention for objectively determining ocular disorders comprises the steps of:

(a) positioning the apparatus or person so that apertures 26 and 27, resepectively correspond to the right and left eye 16 and 17 of the person being examined;

(b) coaxially illuminating the right and left eye 16 and 17, respectively, positioned according to step (a) with collimated light;

(c) retroflecting the collimated light according to step (b); and (d) measuring the relative intensities of the retroflected collimated light according to step (c) so that ocular disorders can be objectively determined.

Step (d) may preferably be practiced by the steps of:

(i) generating an electrical signal proportional to the corresponding intensities of the retroflected collimated light;

(ii) inverting one of the electrical signals generated according to step (i);

(iii) summing the electrical signals generated according to steps (i) and (ii); and (iv) indicating the sum of the electrical signals summed according to step (iii).

Therefore, it will be apparent to one skilled in the art that a quick, efficient and thorough objective screening of a patient's eyes can be obtained utilizing the apparatus and method of the present invention such that ocular disorders can be readily and objectively detected.

While the invention has been herein described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies, structures and methods.

What we claim is:

1. An apparatus for objectively detecting ocular disorders adapted to the expedient examination of uncooperative patients by simultaneously comparing the fundus reflex of each eye and indicating the deviation from normal thereof comprising:

means for collimating light into two predetermined paths for coaxial illumination of a person's right and left eye;

conditioning means acting on the collimated light in said two predetermined paths for conditioning said collimated light to effect modulation thereof;

aperture means disposed at one end of said two predetermined paths for permitting a person's eyes to be illuminated by said collimated light and for permitting retroflection of said collimated light by said person's eyes; and means responsive to the intensity of said retroflected collimated light for detecting the relative intensities of said retroflected collimated light, wherein said detecting means includes:

means for generating an electrical signal proportional to the detected intensity of said retroflected collimated light discretely corresponding to the right and left eye, respectively; and means connected to said generating means for measuring the difference between said electrical signals so that ocular disorders can be objectively detected.

2. An apparatus as recited in claim 1 wherein said collimating means includes:

light source means for providing non-collimated light;

first lens means operatively associated with said light source means for collimating the light from said light source means into said two predetermined paths; and baffle means associated with said first lens means defining an opening to singularly permit light to transmit therethrough.

3. An apparatus as recited in claim 1 wherein said conditioning means includes:

means for splitting said collimated light so that only a portion of said collimated light is transmitted therethrough; and modulating means for modulating the portion of said collimated light transmitted through said splitting means to produce a square wave modulation of said transmitted collimated light.

4. An apparatus as recited in claim 2 wherein said collimating means further includes means operatively associated with said light source means to filter said collimated light.

5. An apparatus as recited in claim 4 wherein said filter means comprises an optical bandpass filter.

6. An apparatus as recited in claim 3 wherein said splitting means is positioned so that the angle of incidence between said collimated light and said splitting means is 45°.

7. An apparatus as recited in claim 3 wherein said conditioning means further includes means to trap the portion of collimated light not transmitted through said splitting means.

8. An apparatus as recited in claim 3 wherein said modulating means comprises:

a circular structure at least a portion of which is interposed between said splitting means and said predetermined paths and extending into the path of said collimated light having a portion of two generally opposing quadrants removed therefrom to define an open area that permits said collimated light to transmit therethrough; and motor means connected to about the central point of said circular structure to effect rotational movement thereto so that said collimated light is square wave modulated by alternatingly transmitting and blocking said collimated light by the portion of said structure extending into the path of said collimated light.

9. An apparatus as recited in claim 1 wherein said aperture means comprises first and second generally circular openings horizontally spaced respectively corresponding to the right and left eye.

10. An apparatus as recited in claim 1 wherein said measuring means comprises:

first and second means to amplify said proportional electrical signals respectively corresponding to the right and left eyes;

means connected to said second amplifying means to invert a predetermined electrical signal associated therewith;

means connected to said first amplifying means and to said inverting means to sum said electrical signals associated therewith; and means connected to said summing means to indicate the numerical sum of said electrical signals.

11. An apparatus as recited in claim 10 wherein said summing means comprises a summing amplifier.

12. An apparatus as recited in claim 10 wherein said indicating means comprises a volt meter.

13. A method for expediently examining uncooperative patients adapted to objectively detecting ocular disorders comprising the steps of:

(a) coaxially illuminating the right and left eye of a patient with collimated light;

(b) effecting a relative position between the apertures of an apparatus and a patient's eyes so that the patient will briefly look into the apertures to effect illuminating contact with the collimated light;

(c) retroflecting the collimated light illuminating each eye according to step (b); and (d) measuring the relative intensities of the retroflected collimated light according to step (c) so that ocular disorders can be objectively determined.

14. A method as recited in claim 13 wherein the collimated light of step (a) is conditioned by rotating a circular structure having a portion of two generally opposing quadrants removed therefrom and at least a portion of which extends into the path of the collimated light.

15. A method as recited in claim 13 wherein step (d) is practiced by the steps of:

(i) generating an electrical signal proportional to the corresponding intensities of the retroflected collimated light;

(ii) inverting one electrical signal generated according to step (i);

(iii) summing the electrical signals generated according to steps (i) and (ii); and (iv) indicating the sum of the electrical signals summed according to step (iii).

16. A method as recited in claim 15 wherein step (i) is practiced by interposing photodetectors into the respective paths of retroflected collimated light corresponding to the right and left eye.

17. A method as recited in claim 15 wherein step (iii) is practiced by utilizing a summing amplifier.

18. A method as recited in claim 12 wherein step (iv) is practiced by utilizing a volt meter.

19. An apparatus as recited in claim 2 wherein said collimating means includes means to forwardly direct light emitted from said light source means.

* * * * *